United States Patent [19]

Seidel et al.

[11] 4,268,639
[45] May 19, 1981

[54] SELF-CURING COMPOSITION BASED UPON POLYMETHYLMETHACRYLATE AND PROCESS FOR MANUFACTURING SAID SELF-CURING COMPOSITION

[76] Inventors: Hartmut Seidel, Hochrad 19; Kurt Polzhofer, Bellmannstr. 8, both of 2000 Hamburg 52, Fed. Rep. of Germany

[21] Appl. No.: 76,925

[22] Filed: Sep. 19, 1979

[30] Foreign Application Priority Data

Oct. 2, 1978 [DE] Fed. Rep. of Germany ....... 2842839

[51] Int. Cl.³ .................... C08F 265/04; C08F 265/06
[52] U.S. Cl. ................................. 525/303; 525/309; 128/92 B
[58] Field of Search .............................. 525/303, 309

[56] References Cited

U.S. PATENT DOCUMENTS 3,446,875  5/1969  Brückmann et al. ............... 525/303
3,468,977  9/1969  Brückmann et al. ............... 525/303

OTHER PUBLICATIONS

Loskaek and Fox, J. Amer. Chem. Soc., vol. 75, p. 3544 (1953).
Oest et al., "Die Knochenzemente", pp. 110–117, 146, 147, 155–156 (1975).

*Primary Examiner*—Carman J. Seccuro
*Attorney, Agent, or Firm*—Cushman, Darby & Cushman

[57] ABSTRACT

Self-curing compositions are prepared based on polymethyl methacrylate (PMMA) are by mixing a finely powdered solid polymer phase of PMMA and/or poly (2-hydroxyethyl methacrylate) (PHEMA) with a liquid monomer phase of methyl methacrylate (MMA) and/or 2-hydroxyethyl methacrylate (HEMA) in a weight ratio of polymer phase to monomer phase of 1.5 to 3.3:1 wherein the portion of PHEMA in the cured product is between 2 and 99 weight %. The product is prepared by vigorously stirring the mixture at room temperature until the polymerization is essentially finished.

21 Claims, No Drawings

SELF-CURING COMPOSITION BASED UPON POLYMETHYLMETHACRYLATE AND PROCESS FOR MANUFACTURING SAID SELF-CURING COMPOSITION

BACKGROUND OF THE INVENTION

The present invention is directed to a self-curing composition based on polymethyl methacrylate (PMMA) which can be used advantageously in bone surgery, as well as to a process for its production.

Self-curing synthetic resins have been known for a long time and have also been used for a long time in operative orthopedy. A material provided for implantation has very special demands placed on it, for example chemical and mechanical stability even under the long time effect of body fluids, biological compatibility, producibility in any desired form, good sterilizability, etc. At the same consideration should be given to the economy and cost worthiness in using such materials. Therefore it is not surprising that the selection of suitable products previously has been limited to only a few types of synthetic resins, of which polymethyl methacrylate has been chiefly used in orthopedic surgery.

Polymethyl methacrylate (PMMA) resins are hard, flexible, colorless, thermoplastic synthetic resins which also withstand severe mechanical loads and which because of their biological compatibility and good sterilizability are suitable for the production of elastic protheses. Thus, e.g. under the trademarks Paladon, Propolat and Palacos PMMA products have long been known as dental protheses synthetic resins or as bone cements for orthopedic surgery. In principle it is a matter of polymer powder which is stirred to a paste with the corresponding monomeric liquid (methyl methacrylate) which, according to the type of further additions, particularly polymerization catalysts hardens to a very solid, homogeneous composition at room temperature or at elevated temperature in a short time.

Although those PMMA products have been employed for a long time in bone surgery, their use is not completely without problems. While a skilled operator in the mixing in and employing of the PMMA bone cement cannot avoid, as the development of heat during the polymerization or the effect of the added MMA monomers on the circulation and the heart function of the patients, as a rule though suitable conditions it can be reduced to an acceptable composition for the patients, it particularly eliminates the procedures which accomplish the steering control of the operator in the bone cement and at the boundary of bone cement and protheses, particularly, however at the bone cement-bone boundary after the implantation. Thus a definite shrinkage of the known, previously employed PMMA polymers in the complete curing cannot be avoided, wherein the shrinkage of the monomer alone during the polymerization alone amounts to about 23% according to Loskaek and Fox, J. Amer. Chem. Soc. Vol. 75, page 3544 (1953). This shrinkage can permanently negatively influence the secure fastening of the protheses in the bone cement as well as the ratio at the bone cement-bone boundary and be important as the cause of numerous failures which occur with increasing frequency with increased interval from the time of implanting the protheses.

The present invention therefore is based on the problem of providing a self-curing synthetic composition which does not have the above mentioned disadvantages and therefor is better suited than previously known synthetic resins as bone cement in the orthopedic surgery.

SUMMARY OF THE INVENTION

According to the invention this problem is solved by producing a self-curing composition based on polymethyl methacrylate (PMMA) which is prepared by mixing a finely powdered solid polymer phase of PMMA and/or poly (2-hydroxyethyl methacrylate) (PHEMA) with a liquid monomer phase of methyl methacrylate (MMA) and/or 2-hydroxyethyl methacrylate in a weight ratio of polymer phase to monomer phase of 1.5 to 3.3:1 wherein the portion of PHEMA in the cured product is between 2 and 99 weight % and wherein optionally further conventional additives such as initiators, X-ray contrast agents, activators, inhibitors and the like can be mixed into one or both phases. The product is prepared by vigorously stirring the mixture at room temperature until polymerization is essentially finished.

It has surprisingly been established that self-curing compositions are obtained through the combination of the invention which quickly lead to a plastic product in the pasting with the corresponding monomers (MMA and/or HEMA) which already after 2 minutes is no longer sticky or adhesive but separates from the support or the hands without residue and therefore in workability and handling differs advantageously from the previously known bone cements which as a rule only reach a consistency 4 minutes after the pasting which is no longer sticky and adhesive. Besides the composition of the invention remains plastic longer, for example it is still workable after 6 minutes without doing anything further. This is of substantial significance for the patients particularly in regard to compatibility since through the possibility of extending the time so far for the filling of the bone cement into the hollow space of the bone until the bone cement already is polymerized to a substantial extent there can be substantially eliminated immediate complications due to large amounts of still present monomer, since the monomer content in the still workable bone cement is already greatly lowered to the time of filling.

Furthermore the self-curing compositions of the invention in regard to changes in volume during the polymerization show in comparison to known bone cements clear superiority. While in the known bone cements in the hardening there occurs totally a contraction in volume (shrinkage), as a result of which late injury can occur at the prostheses, for example a disintegration at the fastening of joint prostheses, the compositions of the invention in contrast thereto show pronounced swelling ability so that after the curing even at body temperature no shrinkage occurs but in contast a swelling through which is guaranteed that the bone cement truly permanently fills the hollow space in the bones to be filled and through the swelling pressure forms a solid fastening both at the cement-bone-boundary and also with the cemented prostheses shrank.

The self-curing compositions of the invention are distinguished accordingly through an improvement of the adhesion of the bone cement both at the prostheses and at the cement-bone-boundary and by a marked swelling ability. For the life of the implanted prostheses and for obtaining an intact bone the latter is not of underrated significance. It is known that each bone uses for building up and maintenance a certain contact pressure as a growth stimulant, of which for example use is made in the principle of the elastic locking with the Kinchrer nail. In similar manner through the composition of the invention if it is employed as bone cement because of its capability for swelling in combination with the body liquids there is exerted a decided pressure on the bone surrounding it (and the cemented prostheses shank), which likewise operates as growth stimulating and can lead to a (desired) strengthening of the bone wall in a natural manner. A corresponding positive effect with the previously known comparable bone cements is not produced since differing from the composition of the invention they are based on a distinctly shrinking process and therefore can exert no pressure on their surroundings.

Preferably the weight ratio of polymer phase to monomer phase is in the range of 2.0 to 3.0. The polymer phase is suitably present in the form of a fine powder, preferably with an average particle size of 0.1 micron to 0.5 mm.

The further improved properties of the self-curing compositions of the invention explained in detail below are produced by combination of PMMA with HEMA or PHEMA. The weight ratio of PHEMA and PMMA in the cured composition indeed is not critical, however, the portion of PHEMA should suitably be in the range between 2 weight % and 99 weight %. In a particularly preferred form of the invention the polymer phase consists of a mixture of PMMA and PHEMA in the weight ratio of 3.3 to 10:1 and the monomer phase of MMA.

In a further preferred form the self-curing composition of the invention consists of a monomer phase which contains MMA and HEMA in the weight ratio of 0.2 to 1.5:1, and a polymer phase of PMMA and/or PHEMA.

The production of the self-curing composition of the invention takes place analogous to the known bone cements based on PMMA. In this connection there is started with sterile, fine powdered polymer phase which besides the main constituents PMMA and PHEMA can contain further additives such as initiators, x-ray contrast agent, pigments, antibiotics and the like in balanced amounts. For the working up as bone cement it goes without saying sterile conditions are to be maintained. The monomer phase consists of liquid MMA and/or HEMA, to which there can be added further additives such as activators, inhibitors and the like. Polymer and monomer phase are mixed together in specified dosages whereby suitably the powder is introduced in portions in a short time in the liquid and vigorously stirred. There is obtained a kneadable, plastic shapable paste which begins to cure after about 2 minutes. The curing (and therewith the polymerization) is generally completed after about 10 minutes. The bone cement remains plastic about 6 minutes, so that it can be handled sufficiently long, for example for cementation of endoprostheses. Suitably the introduction of the plastic materials takes place first shortly before the complete curing, since there the greatest part of the monomers is already polymerized and perhaps disadvantageous actions of the monomers on the condition of the patients, e.g. drop in blood pressure, slowing of the heart and breath frequency, etc. can be avoided with certainty.

Correspondingly the process of the invention for the production of a self-curing composition based on PMMA is characterized by mixing a finely powdered, solid polymer phase of polymethyl methacrylate and/or poly (2-hydroxyethyl methacrylate) with a liquid monomer phase of methyl methacrylate and/or 2-hydroxyethyl methacrylate in a weight ratio of polymer phase to monomer phase of 1.5 to 3.3:1, whereby the mixture is so chosen that the portion of PHEMA in the cured product is 2 weight % to 99 weight % and whereby in a given case there can be mixed into one or both phases in addition customary additives such as initiators, x-ray contrast agents, activators, inhibitors and the like, the mixture vigorously stirred at room temperature and held at this temperature until the polymerization is substantially completed.

Preferably polymer phase and monomer phase are employed in the weight ratio of 2.0 to 3.0:1. The polymer phase is suitably used in finely powdered form, whereby an average particle size of 0.1 micron to 0.5 mm is preferably employed.

In a particular form of the invention the process is carried out with a mixture of PMMA and PHEMA in the weight ratio of 3.3. to 10:1 as the polymer phase and with MMA as the monomer phase.

In an additional, likewise preferred form of the process of the invention there is employed as the monomer phase a mixture of MMA and HEMA in the weight ratio of 0.2 to 1.5:1 and as the polymer phase PMMA and/or PHEMA.

The composition can comprise, consist essentially of or consist of the materials set forth and the process can comprise, consist essentially of or consist of the steps set forth with such materials.

Unless otherwise indicated all parts and percentages are by weight.

DESCRIPTION OF COMPARISON EXAMPLE AND PREFERRED EMBODIMENT

Example 1 (Comparison Example) p A self-curing composition known as a bone cement was produced as follows:

40 grams of polymethyl methacrylate (PMMA) with about 15 weight % zirconium dioxide (so-called "Palacos R" of the firm Kulzer & Co GmbH, Bad Homburg) and about 0.5 weight % of dibenzoyl peroxide as catalyst formed the solid phase and was added to 20 grams of methyl methacrylate (MMA) (density: 0.9433 at 20° C.) with 0.7 weight % of N,N-dimethyl-p-toluidine as cocatalyst and 0.006 weight % hydroquinone and chlorophyll as the liquid phase and the components mixed under vigorous stirring at room temperature (24° C.) whereby there was obtained a plastic, shapable composition with the development of heat.

This plastic composition was worked up at a room and material temperature of 24° C. as bone cement for filling in the cleaned out marrow cavity of a bone, as soon as it had formed a kneadable paste. This was the case about one minute after beginning of the mixing, whereby the composition was still viscous and not free from adhesives. The workability ended after about 3 to 4 minutes, since at this time the composition was rubbery elastic.

EXAMPLE 2

A self-curing composition according to the invention was produced as follows:

A solid phase of 33.80 grams of a bead shaped, commercial polymethyl methacrylate having a particle size in the range of 0.01 to 0.1 mm 6.00 grams of zirconium dioxide as x-ray contrast agent
10.00 grams of poly (2-hydroxyethyl methacrylate) (PHEMA) with a particle size in the range of 0.1 to 0.5 mm and
0.2 grams of dibenzoyl peroxide as catalyst were introduced into a liquid phase of
20.00 grams of methyl methacrylate containing 0.5 weight % N,N-dimethyl-p-toluidine and 0.005 weight % hydroquinone and worked up in the manner given in Example 1.

The working up as bone cement was likewise possible at room and material temperature of 24° C. 1 minute after the beginning of mixing, whereby the composition was neither viscous nor adhesive but rather was easily separated without residue from the support, the instruments and rubber gloves. The workability was still possible 6 minutes later without doing anything else and ended after about 7 to 8 minutes.

EXAMPLES 3 to 5

In the same manner as described in Example 1 self-curing compositions according to the invention were produced based on the composition of the solid and liquid phase as set forth in Example 2 with the difference that the solid phase contained changing amounts of poly (2-hydroxyethyl methacrylate) (PHEMA), namely in Example 3, 3.50 grams PHEMA, in Example 4, 5.50 grams PHEMA and in Example 5, 7.50 grams PHEMA. In all cases a composition was obtained which could be worked up as bone cement in the same manner and in the same working time as stated in Example 2.

Example 6

A self-curing composition according to the invention from a solid phase having 49.5 grams of PHEMA and 0.5 grams of dibenzoyl peroxide and a liquid phase of 20 grams of 2-hydroxyethyl methacrylate (HEMA) containing 0.7 weight % of N,N-dimethyl-p-toluidine was produced and worked up as a bone cement as described in Example 2. The composition obtained was worked up in the same manner and in the same working time (about 6 minutes) as stated in Example 2.

Example 7

A self-curing composition according to the invention from a solid phase which had the composition stated in Example 1 and a liquid phase of 20 grams HEMA having 0.7 weight % N,N-dimethyl-p-toluidine was produced and worked up according to Example 2. It showed a similar good workability in the same working time as stated in Example 2.

Example 8

A self-curing composition according to the invention from a solid phase which had the composition stated in Example 2 and a liquid phase with the composition set forth in Example 6 was produced and tested according to Example 2. It showed a similar good workability in the same working time as stated in Example 2.

Example 9

The procedure was the same as in Example 2 except that the solid phase was composed as in Example 6 and the 20 gram liquid phase consisted of 83 weight % HEMA, 16.3 weight % MMA and 0.7 weight % N,N-dimethyl-p-toluidine. The thus produced composition also was able to be worked up in the time period given in Example 2 without difficulty.

Example 10

The procedure was the same as in Example 2 except that the solid phase was composed as in Example 1 and the 20 gram liquid phase consisted of 50 weight % HEMA, 49.3 weight % MMA and 0.7 weight % N,N-dimethyl-p-toluidine. The thus produced composition behaved in regard to workability as stated in Example 2.

Example 11

The procedure was the same as in Example 2 except that the solid phase was composed as in Example 1 and the liquid phase had the composition of Example 9. The thus produced self-curing composition also behaved in regard to workability as stated in Example 2.

The following investigations for determination of the mechanical properties of self-curing compositions of different composition were carried out as far as possible under similar physical surrounding conditions. The test productions, the test shapes and test measurements correspond to the directions which are described in the monograph of O. Oest, K. Muller and W. Hupfauer, "Die Knochenzemente", Stuttgart 1975 pages 110 et seq. Correspondingly for determination of tensile strength according to DIN No. 53455 (German Industrial Standard No. 53455) and elongation at break (likewise according to DIN No. 53455) there were used as test articles so-called "shoulder rods", (dumb-bells) i.e. prismatic rods with parallel gauge lengths and broadening at both ends in the form of a "shoulder" which were produced in test shape No. 3 according to DIN 53455 and whose average testing part parallel gauge lengths had the dimensions 60 mm × 10 mm × 3 to 4 mm. For the arrangement of the experiment see, e.g. O. Oest et al., "Knochenzemente", Stuttgart 1975 page 147 illustrations 8.41 and 8.42.

The compression stress, i.e. the behavior of the bone cements with application of a compressive load was determined according to DIN 53454 with cylindrical test articles which are 12 mm long and 10 mm in diameter. The arrangement of the experiment was described in the above cited monograph "Knochenzemente", pages 155–156 illustrations 8.51 and 8.52.

The determination of adhesive strength took place with the help of penetration experiments in which cylindrical ceramic tubes filled with bone cement compositions were employed as test articles. The detailed description of the arrangement of the experiment is given below before Table 2.

There were used standard small roads for the measurement of the modulus of elasticity according to DIN No. 53457, which were produced in test shape 2 according to DIN No. 53452, with the dimension 50 mm × 6 mm × 4 mm.

All measurements were carried out with a tensile testing machine (Type 1547, manufacturer, firm K. Frank Weinheim).

The collected results set forth in the following Table I are average values, in each case of 10 measurements.

TABLE I

Mechanical Properties of (a) A Known PMMA Bone Cement (Palacos) and (b) That of The Composition of the Invention Produced According to Example 2

| Experiment Nr. | Measured mech. Property (Dimension) | Known PMMA-Bone Cement (According to Ex. 1) | | PMMA/PHEMA/MMA Cement (According to Ex. 2) | |
|---|---|---|---|---|---|
| | | unswollen* | swollen** | unswollen* | swollen** |
| 1 | tensile strength (N mm$^{-2}$) | 44.3 ± 4.0 | 44.4 ± 1.6 | 34.5 ± 1.5 | 34.4 ± 2.2 |
| 2 | elongation at break (%) | 3.3 ± 0.4 | 3.6 ± 0.3 | 2.5 ± 0.2 | 3.6 ± 0.4 |
| 3 | compressive stress (N mm$^{-2}$) | 99.9 ± 3.2 | 97.8 ± 6.0 | 93.6 ± 3.6 | 87.2 ± 4.1 |
| 4 | adhesive strength (N) | 250 ± 390 | 370 ± 240 | 750 ± 650 | 1650 ± 460 |
| 5 | modulus of elasticity (N mm$^{-2}$) | 1644 ± 70 | 1590 ± 140 | 1650 ± 120 | 1170 ± 100 |

*measured after one day storage at 20 degrees C. and 65% relative humidity
**measured after one day swelling at 20 degrees C. in Ringer solution The results in Table I show very clearly that the measured mechanical properties of the composition of the invention do not differ substantially from the known bone cements up to the adhesive strength. In the adhesive strength the difference is unusually large both in the swollen condition and also in the unswollen condition; the composition of the invention in the unswollen state adheres about three times stronger than the known bone cement, in the swollen state it adheres about four times stronger than the known bone cement.

In the following Table 2 there are collected the results of adhesive strength measurements which were ascertained with the help of penetration experiments. For this purpose 25 mm long porous ceramic tubes (Degussa) with an outer diameter of 26 mm and an inner diameter of 18 mm were filled with the bone cement composition being tested and stored in the air at 65% relative humidity as well as in a parallel test stored simultaneously at 20° C. Thereby two series of experiments were carried out one with a storage time of one day, the second with a storage time of 28 days. Subsequently the samples were tested in a tensile strength testing machine (manufacturer K. Frank GmbH, Mannheim) with a draw speed of 10 mm/min. Thereby the cement filling was forced out of the ceramic tube with the help of a metal punch. The maximum strength which was required to penetrate the cement filling was measured and served as a measure of the bond strength of the investigated bone cement compositions to the ceramic surface.

TABLE II

BOND STRENGTH OF BONE CEMENTS TO A POROUS CERAMIC WALL

| FROM EXAMPLE | BONE CEMENT SAMPLES COMPOSITION | STORAGE TIME DAYS | STORAGE AT 20° C. | BOND STRENGTH LOAD |
|---|---|---|---|---|
| 1 | PMMA/MMA (known composition) | 1 | 65 rel. Hum. | 1290 ± 350 |
| 2 | PMMA/PHEMA/MMA | 1 | 65 rel. Hum. | 1380 ± 590 |
| 5 | PMMA/PHEMA/MMA | 1 | 65 rel. Hum. | 1570 ± 750 |
| 1 | PMMA/MMA (known composition) | 28 | 65 rel. Hum. | 1080 ± 447 |
| 2 | PMMA/PHEMA MMA | 28 | 65 rel. Hum. | 1879 ± 536 |
| 6 | PHEMA/HEMA | 28 | 65 rel. Hum. | 4242 ± 3019 |
| 8 | PMMA/PHEMA/HEMA | 28 | 65 rel. Hum. | 567 ± 148 |
| 1 | PMMA/MMA (known composition) | 1 | Ringer solution | 158 ± 37 |
| 2 | PMMA/PHEMA/MMA | 1 | Ringer solution | 1070 ± 187 |
| 5 | PMMA/PHEMA/MMA | 1 | Ringer solution | 721 ± 250 |
| 1 | PMMA/MMA (known composition) | 28 | Ringer solution | 146 ± 53 |
| 2 | PMMA/PHEMA/MMA | 28 | Ringer solution | 1216 ± 574 |
| 7 | PMMA/HEMA | 28 | Ringer solution | 3524 ± 474 |
| 8 | PMMA/PHEMA/HEMA | 28 | Ringer solution | 3348 ± 545 |

All values were the averages of 10 determinations

From Table II it can be seen that the compositions of the invention both after 1 day storage and also especially marked after 28 days swelling in Ringer's solution at 20° C. showed a substantially higher bond strength than the known bone cement "Palacos".

As has already been explained in detail above the self-curing compositions of the invention are distinguished by a marked capacity for swelling, on which obviously at least in part the advantages rest which are obtained in the use of these compositions as bone cement in regard to capability of functions and duration of implanted prostheses.

For the determination of the swelling behavior there were used as bone cement-test articles standard small rods conforming to test form 2 according to DIN No. 53452 with a length of 50 mm, a width of 6 mm and a height of 4 mm both of a known bone cement made of PMMA/MMA (Palacos) and also made of the composition PMMA/PHEMA/MMA of the invention and produced according to Example 2. The standard small rods obtained were placed in Ringer's solution at 20° C. in such a manner that they were completely covered. After fixed intervals of time the respective changes in weight of the test articles were determined. The results are collected in Table 3 and reveal that the increase in weight (through water absorption) in dependence on the swelling time is a characteristic of the swelling behavior of the bone cement in question. Accordingly the swelling capacity of the compositions of the invention is about 2.5 times greater than the known bone cement investigated.

| Swelling Time (in Weeks) | Known Composition PMMA/MMA (According to Example 1) | Composition According to the Invention PMMA/PHEMA/MMA (According to Example 2) |
|---|---|---|
| 0.5 | 0.8 | 1.6 |
| 1 | 1.3 | 2.6 |
| 2 | 1.3 | 3.0 |
| 3 | 1.4 | 3.3 |
| 4 | 1.4 | 3.7 |
| 5 | 1.5 | 4.1 |
| 6 | 1.6 | 4.4 |
| 7 | 1.7 | 4.7 |
| 8 | 1.7 | 4.7 |
| 9 | 1.7 | 4.8 |
| 10 | 1.7 | 4.9 |
| 11 | 1.7 | 4.9 |
| 12 | 1.8 | 5.0 |

As is known a material capable of swelling expands in the swelling and thereby exerts a certain swelling pressure on its surroundings so far as it is prevented from expansion. Since, as described above, the development of a swelling pressure by a bone cement swelling in the presence of body liquids can effect a strengthening of the bones through growth stimulation, through which the bones are strengthened and made resistant against mechanical loads which, in turn influences the ability to function and life span of the prostheses in a positive manner, the knowledge of the swelling pressure is important for judging the quality of the bone cements.

To determine the swelling pressure of the bone cement cylindrical, molded test articles 30 mm long and 24 mm diameter were placed in a perforated metal jacket and held at the ends of the metal jacket by means of screw expellers. In one of the two screw expellers there was built in a pressure measuring dosage with a measuring range of 0 to 50 bar. With the second screw expeller which had a fine thread there was established at the beginning of the experiment an inlet pressure of about 1 bar. The thus prepared samples were placed in Ringer's solution having a temperature of 20° C. so that they were completely covered by the solution and remained a fixed length of time in the solution.

The increasing pressure through swelling of the test articles was recorded continuously.

As test articles there were investigated a known bone cement according to Example 1 (Palacos) and a self-curing composition of the invention compounded according to Example 2 (PMMA/PHEMA/MMA). The results are collected in Tables IVa and IVb.

TABLE IVa

| | Swelling Pressure of Bone Cements at 20° C. | |
|---|---|---|
| Swelling Time (hours) | Swelling Pressure PMMA/MMA (According to Ex. 1) | (in bar) of PMMA/PHEMA/MMA (According to Ex. 2) |
| 0 | 1.0 (inlet pressure) | 1.0 (inlet pressure) |
| 2 | 1.0 | 1.6 |
| 4 | 1.1 | 2.1 |
| 6 | 1.2 | 2.4 |
| 8 | 1.25 | 2.5 |
| 10 | 1.25 | 2.5 |
| 12 | 1.25 | 2.6 |
| 14 | 1.25 | 2.65 |
| 16 | 1.25 | 2.75 |
| 18 | 1.25 | 2.8 |
| 20 | 1.25 | 2.85 |
| 22 | 1.3 | 2.9 |
| 24 | 1.3 | 3.0 |

TABLE IVb

| Swelling Pressure of PMMA/PHEMA/MMA (According to Example 2) (Long Time Experiment) | | | |
|---|---|---|---|
| Swelling Time | Swelling Pressure | Swelling Time | Swelling Pressure |
| 0 | 1 (inlet pressure) | 8 | 19.5 |
| 1 | 4.8 | 9 | 21.0 |
| 2 | 8.5 | 10 | 22.5 |
| 3 | 11.0 | 11 | 24.0 |
| 4 | 12.5 | 12 | 25.0 |
| 5 | 14.5 | 13 | 26.5 |
| 6 | 16.5 | 14 | 27.5 |
| 7 | 18.0 | 15 | 28.5 |

The measured results set forth in Tables IVa and IVb are average values, in each case of 10 experiments.

The results in Tables IVa very plainly show the substantially stronger swelling pressure of the composition of the invention in which after 4 hours there is already about double as large a pressure as the previously established pressure while in the same time the known bone cement composition had built up no mentionáble swelling pressure. After 24 hours the swelling pressure of the composition of the invention had already increased three times while for the known bone cement it was only ⅓ over the inlet pressure.

Table IVb shows that the swelling pressure of the composition of the invention even over four weeks continuously increased further and thereby reached values which were sufficient to exert a noticeable effect on the surrounding bone in use as a bone cement.

The entire disclosure of German priority application P No. b 28428319 is hereby incorporated by reference.

What is claimed is:

1. A self-curing composition prepared by mixing a finely powdered solid polymer phase comprising a polymeric alkyl methacrylate with a liquid monomer phase comprising monomeric alkyl methacrylates, the polymer and monomer of the composition mixture is a combination consisting essentially of:

(1) Polymethyl methacrylate, monomeric 2-hydroxyethyl methacrylate or (2) Polymethyl methacrylate + poly-(2-hydroxyethyl methacrylate), monomeric 2-hydroxyethyl methacrylate or (3) Polymethyl methacrylate + poly-(2-hydroxyethyl methacrylate), monomeric 2-hydroxyethyl methacrylate + monomeric methyl methacrylate or (4) Polymethyl methacrylate + poly-(2-hydroxyethyl methacrylate), monomeric methyl methacrylate or (5) Poly-2-(hydroxyethyl methacrylate), monomeric-2-hydroxyethyl methacrylate or (6) Poly-(2-hydroxyethyl methacrylate), monomeric methyl methacrylate or (7) Poly-2-(hydroxyethyl methacrylate), monomeric 2-hydroxyethyl methacrylate + monomeric methyl methacrylate, wherein the weight ratio of polymer phase to monomer phase is in the range of 1.5 to 3.3:1 and wherein the portion of poly-2-(hydroxyethyl methacrylate) in the cured product is at least 2% by weight and at most 99% by weight, and then vigorously stirring said mixture at room temperature until polymerization is essentially finished.

2. A composition according to claim 1 wherein the weight ratio of polymer phase to monomer phase is in the range of 2.0 to 3.0:1.

3. A composition according to claim 1 wherein the average particle size of the polymer phase is from 0.1 micron to 0.5 mm.

4. A composition according to claim 3 wherein the polymer phase consists essentially of polymethyl methacrylate and poly (2-hydroxyethyl methacrylate) in the weight ratio of 3.3 to 10:1 and the monomer phase consists essentially of methyl methacrylate.

5. A composition according to claim 2 wherein the polymer phase consists esentially of polymethyl methacrylate and poly (2-hydroxyethyl methacrylate) in the weight ratio of 3.3 to 10:1 and the monomer phase consists essentially of methyl methacrylate.

6. A composition according to claim 1 wherein the polymer phase consists essentially of polymethyl methacrylate and poly (2-hydroxyethyl methacrylate) in the weight ratio of 3.3 to 10:1 and the monomer phase consists essentially of methyl methacrylate.

7. A composition according to claim 3 wherein the monomer consists essentially of a mixture of methyl methacrylate and 2-hydroxyethyl methacrylate in the weight ratio of 0.2 to 1.5:1 and the polymer phase consists essentially of (1) polymethyl methacrylate, (2) poly-(2-hydroxyethyl methacrylate) or (3) a mixture of polymethyl methacrylate and poly (2-hydroxyethyl methacrylate).

8. A composition according to claim 2 wherein the monomer consists essentially of a mixture of methyl methacrylate and 2-hydroxyethyl methacrylate in the weight ratio of 0.2 to 1.5:1 and the polymer phase consists essentially of (1) polymethyl methacrylate, (2) poly-(2-hydroxyethyl methacrylate) or (3) a mixture of polymethyl methacrylate and poly (2-hydroxyethyl methacrylate).

9. A composition according to claim 1 wherein the monomer consists essentially of a mixture of methyl methacrylate and 2-hydroxyethyl methacrylate in the weight ratio of 0.2 to 1.5:1 and the polymer phase consists essentially of (1) poly-methyl methacrylate, (2) poly-(2-hydroxyethyl methacrylate) or (3) a mixture of polymethyl methacrylate and poly (2-hydroxyethyl methacrylate).

10. A process of preparing the self-curing composition of claim 1 comprising mixing a finely powdered polymer phase wherein the polymer is (1) polymethyl methacrylate (2) poly (2-hydroxyethyl methacrylate) or (3) a mixture of polymethyl methacrylate and poly (2-hydroxyethyl methacrylate) with a liquid polymerizable monomer phase wherein the monomer is (1) methyl methacrylate, (2) 2-hydroxyethyl methacrylate and 2-hydroxyethyl methacrylate in a weight ratio of polymer phase to monomer phases of 1.5 to 3.3:1 and vigorously stirring the mixture at room temperature until the polymerization is substantially complete.

11. A process according to claim 10 wherein the polymer phase is added in an average particle size of 0.1 microns to 0.5 mm.

12. A process according to claim 11 wherein the polymer phase and the monomer phase are employed in the weight ratio of 2.0 to 3.0:1.

13. A process according to claim 12 wherein the mononer phase consists essentially of a mixture of methyl methacrylate and 2-hydroxyethyl methacrylate in the weight ratio of 0.2 to 1.5:1 and the polymer phase consists essentially of (1) polymethyl methacrylate, (2) poly-(2-hydroxyethyl methacrylate) or (3) a mixture of polymethyl methacrylate and poly (2-hydroxyethyl methacrylate).

14. A process comprising applying the composition of claim 1 in surgery or orthopedy to a bone as a bone cement.

15. A process according to claim 14 wherein the weight ratio of polymer phase to monomer phase is in the range of 2.0 to 3.0:1.

16. A process according to claim 14 wherein the average particles size of the polymer phase is from 0.1 micron to 0.5 mm.

17. A process according to claim 16 wherein the polymer phase consists essentially of polymethyl methacrylate and poly (2-hydroxyethyl methacrylate) in the weight ratio of 3.3 to 10:1 and the monomer phase consists essentially of methyl methacrylate.

18. A process according to claim 16 wherein the monomer consists essentially of a mixture of methyl methacrylate and 2-hydroxyethyl methacrylate in the weight ratio of 0.2 to 1.5:1 and the polymer phase consists essentially of (1) polymethyl methacrylate, (2) poly-(2-hydroxyethyl methacrylate) or (3) a mixture of polymethyl methacrylate and poly (2-hydroxyethyl methacrylate).

19. A composition according to claim 1 which is capable of being completely cured in about 10 minutes.

20. A process according to claim 10 wherein the polymerization is carried to completion within a time of about 10 minutes.

21. A process according to claim 14 wherein the bone cement is one which retains its plasticity and workability for 6 to 8 minutes.

* * * * *